June 14, 1960 E. PRUSHEK Plant Pat. 1,953
CHRYSANTHEMUM PLANT
Filed Dec. 17, 1958
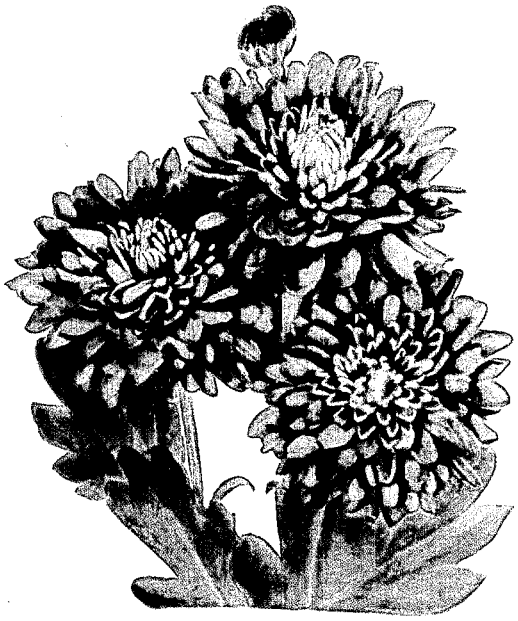
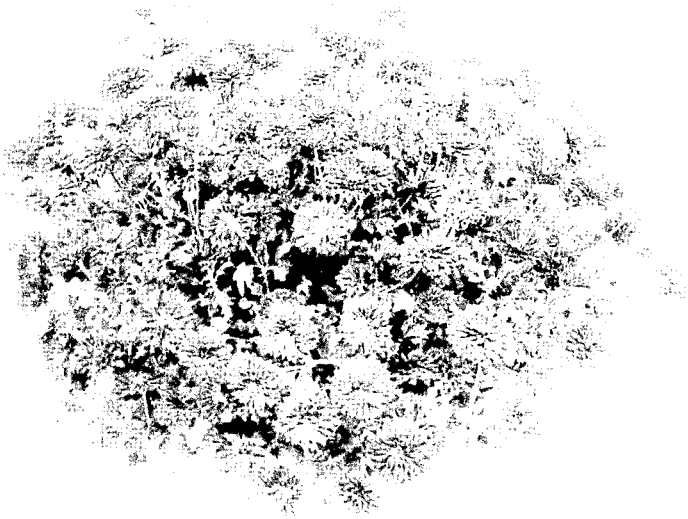
Emil Prushek
INVENTOR.
BY Robb & Robb
attorneys.

United States Patent Office

Plant Pat. 1,953
Patented June 14, 1960

1,953

CHRYSANTHEMUM PLANT

Emil Prushek, Niles, Mich., assignor to R. M. Kellogg Company, Three Rivers, Mich., a corporation of Michigan Filed Dec. 17, 1958, Ser. No. 781,173
1 Claim. (Cl. 47—60)

My present invention comprises a new and distinct variety of chrysanthemum plant, the result of crossing two unnamed seedlings.

The principal object of my invention was to produce a new variety of chrysanthemum plant of the cushion-type having blossoms of a satisfactory and lasting red color with an earlier and longer blooming period.

Satisfactory red chrysanthemums have been difficult to develop in view of the fact that red color and lateness of blooming have heretofore seemed to be linked characteristics of chrysanthemum plants.

The development of the present new variety has resulted from a program which I have been conducting of careful selection and cross breeding with the view of producing new varieties of chrysanthemums of the cushion type having more dwarf and compact habits of growth, and having different desired colors in reference to the blooms of such plants.

The result of the specific hybridization above mentioned has been to produce my present new and distinct variety of chrysanthemum plant, characterized by the ox blood red color of its blooms, its smaller and more compact blooms having a more double arrangement of its petals and few stamens, its dwarfer and more compact habit of growth, and its earlier and longer blooming period.

While my new variety bears a closer resemblance to the unpatented variety "Santa Claus" than it does to other known varieties, it differs from such known varieties in respect of the characteristics hereinbefore enumerated. The physical structure of the blooms of my new variety is closer to a pom-pon type.

My new variety has been found to retain its distinctive characteristics through successive asexual reproduction.

The accompanying drawing forming a part hereof shows a typical plant of my new variety of chrysanthemum.

Asexual reproduction has been accomplished by means of cuttings in the vicinity of Niles, Michigan.

The following is a detailed description of my new variety of chysanthemum plant:

Parentage: Seedling.
Classification: Botanic—*Chrysanthemum bortorum.*

*Flower*

(Observations made October 17 from a plant that was grown in the field at Niles, Michigan, U.S.A.)

Blooming: habit: Blooms profusely and continuously mid-season in Fall beginning about September 15th to 20th and continuing to about November 1st to 10th.

Bud:
- *Size.*—Medium.
- *Form.*—Short with flat top; is not affected by wet or hot weather.
- *Color.*—When sepals first divide—Ox Blood Red, Plate 823/1. When petals begin to unfurl—Ox Blood Red, Plate 823/2. When half blown: inside of petals—Ox Blood Red, Plate 823/3. Reverse of petals—same coloring. (Above color references are to the Horticultural Colour Chart of the British Colour Council.)
- *Sepals.*—Smooth edge.
- *Calyx.*—Shape—apple; size—small; aspect—smooth.

- *Peduncle.*—Short; aspect—rough; color—bronzy; strength—erect, heavy. Opening—bud opens well and is not affected by adverse weather conditions.

Bloom:
- *Size.*—Small; average size when fully expanded—1¾ inches.
- *Borne.*—Several together—irregular.
- *Stems.*—Short; strong.
- *Form.*—When first opened—globular; permanence—retains its form to the end.
- *Petalage.*—Very double; number of petals under normal conditions—about 160.
- *Color.*—New flower—outer petals: Face—Ox Blood Red, Plate I; reverse—Pompeian Red, Plate XIII. Intermediate petals: Face—Brazil Red, Plate I; reverse—Dragon's Blood Red, Plate XIII. Center petals: Face—Maroon, Plate I, in depth blending into Brazil Red, Plate I, at top. Older Bloom—Outer petals: Face—Ox Blood Red, Plate I; reverse—Pompeian Red, Plate XII. Intermediate petals: Face—Garnet Brown, Plate I; reverse—Dragon's Blood Red, Plate XIII. Center petals: Face—Maroon, Plate I, in depth blending into Brazil Red, Plate I, at top; reverse—Light Salmon-Orange, Plate II.
- *General tonality from a distance.*—Ox Blood Red, Plate I.
- *Anthers.*—Apricot Yellow, Plate IV.
- *Leaves.*—Dull Blackish Green, Plate XLI, highlighted with Elm Green, Plate XVII.
- *Stem.*—Blended tones of Cress Green, Plate XXXI, and Dark Green, Plate XXXI. (Above color references are to Ridgway Color Chart.)

Petals:
- *Texture.*—Thin; soft. Not affected by wet or hot weather.
- *Appearance.*—Inside—shiny; outside—shiny.
- *Form.*—Oval.
- *Arrangement.*—Irregular.
- *Persistence.*—Hang on and dry.
- *Lastingness.*—On the plant—long. As a cut flower—fair.

*Plant*

Form: Bush; average diameter of plant—15"; average height—10" to 12".

Growth: Vigorous; dwarf; compact.

Foliage:
- *Size.*—Medium.
- *Quantity.*—Normal.
- *Color (new foliage).*—Upper side—normal green; under side—light green.
- *Shape.*—Oval pointed.
- *Texture.*—Velvety; ribs and veins—light.
- *Edge.*—Serrated (saw toothed).
- *Serration.*—Double.
- *Leaf Stem.*—Color—green.
- *Stipules.*—Short; serrated.

Wood:
- *New Wood.*—Color—brown.
- *Bark.*—Rough.
- *Old Wood.*—Color—brown.
- *Bark.*—Rough.

I claim:

A new and distinct variety of chrysanthemum plant, substantially as shown and described, characterized by the Ox Blood Red color of its bloom, its smaller and more compact bloom, a more double arrangement of its petals, its dwarfer and more compact habit of growth, and its earlier and longer blooming season.

No references cited.